US012577377B2

(12) United States Patent
Kida et al.

(10) Patent No.: US 12,577,377 B2
(45) Date of Patent: Mar. 17, 2026

(54) MEDICAL RUBBER COMPOSITION, MEDICAL RUBBER PART, AND PACKAGING ARTICLE FOR MEDICAL RUBBER PART

(71) Applicant: Sumitomo Rubber Industries, Ltd., Kobe (JP)

(72) Inventors: Yogun Kida, Kobe (JP); Kei Tajima, Kobe (JP); Kazuki Nojiri, Kobe (JP); Yuichiro Matsutani, Kobe (JP); Toshiki Onishi, Kobe (JP); Toshikazu Kondo, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 607 days.

(21) Appl. No.: 18/085,605

(22) Filed: Dec. 21, 2022

(65) Prior Publication Data

US 2023/0192996 A1 Jun. 22, 2023

(30) Foreign Application Priority Data

Dec. 22, 2021 (JP) ................................ 2021-208610

(51) Int. Cl.

| | |
|---|---|
| ***C08L 9/00*** | (2006.01) |
| ***A61L 2/08*** | (2006.01) |
| ***A61L 2/081*** | (2026.01) |
| ***C08K 3/04*** | (2006.01) |
| ***C08K 3/22*** | (2006.01) |
| ***C08K 3/34*** | (2006.01) |
| ***C08K 3/36*** | (2006.01) |
| ***C08K 5/3492*** | (2006.01) |
| ***C08K 13/02*** | (2006.01) |

(52) U.S. Cl.

CPC ................ *C08L 9/00* (2013.01); *A61L 2/081* (2013.01); *C08K 13/02* (2013.01); *A61L 2202/18* (2013.01); *A61L 2202/24* (2013.01); *C08K 3/04* (2013.01); *C08K 2003/222* (2013.01); *C08K 2003/2241* (2013.01); *C08K 2003/343* (2013.01); *C08K 3/36* (2013.01); *C08K 5/3492* (2013.01); *C08L 2205/025* (2013.01); *C08L 2205/03* (2013.01); *C08L 2207/062* (2013.01); *C08L 2207/066* (2013.01); *C08L 2312/00* (2013.01)

(58) Field of Classification Search

None

See application file for complete search history.

(56) References Cited

U.S. PATENT DOCUMENTS

2017/0296757 A1* 10/2017 Maeda ................ A61M 5/3202

FOREIGN PATENT DOCUMENTS

| | | | | |
|---|---|---|---|---|
| EP | 841374 A2 * | 5/1998 | ............ | C08K 5/372 |
| JP | H10-179690 A | 7/1998 | | |
| JP | 2002-301133 A | 10/2002 | | |
| JP | 2017-531604 A | 10/2017 | | |

* cited by examiner

*Primary Examiner* — Katarzyna I Kolb

(74) *Attorney, Agent, or Firm* — XSENSUS LLP

(57) ABSTRACT

A medical rubber part in which non-elution characteristics are maintained even after sterilization with gamma ray, a packaging article for the medical rubber part, and a medical rubber composition for manufacturing the medical rubber part can be provided or implemented. The medical rubber composition can contain or comprise: a (a) base polymer containing a halogenated isobutylene-isoprene rubber; a (b) polyethylene; and a (c) triazine derivative as a crosslinking agent. A proportion of the triazine derivative contained per 100% by mole of a halogen of the halogenated isobutylene-isoprene rubber contained in the (a) base polymer can be 1% by mole to 15% by mole.

13 Claims, 3 Drawing Sheets

MEDICAL RUBBER COMPOSITION, MEDICAL RUBBER PART, AND PACKAGING ARTICLE FOR MEDICAL RUBBER PART

CROSS-REFERENCE TO RELATED APPLICATION(S)

The present application claims priority to Japanese Patent App. No. 2021-208610 filed Dec. 22, 2021, wherein the entire content and disclosure of which is incorporated herein by reference.

BACKGROUND

Field

The present disclosure relates to a medical rubber composition for sterilization with gamma ray, a medical rubber part sterilized with gamma ray, and a packaging article for the medical rubber part.

Background Art

Medical rubber plugs for sealing an opening of a syringe, a vial, or the like may be required to have many characteristics such as non-elution characteristics, high cleanability, chemical resistance, resistance to needle piercing, self-sealability, and high slidability. Quality characteristics that may be required of the medical rubber plugs should (or may be required to), in terms of use of the medical rubber plugs, comply with the regulations stipulated in "Test for Rubber Closure for Aqueous Infusions" of the 17th edition of the Japanese Pharmacopoeia, as an example.

For example, Japanese Laid-Open Patent Publication No. H10-179690 describes a rubber plug for a pharmaceutical agent container, the rubber plug being obtained by blending 5 to 25 parts by weight of fine powder of ultrahigh-molecular-weight polyethylene per 100 parts by weight of halogenated isobutylene-isoprene rubber, and vulcanizing the resultant halogenated isobutylene-isoprene rubber by using at least one of 2-substituted-4,6-dithiol-s-triazine derivatives or by using an organic peroxide, in the absence of a zinc compound.

There is an increasing demand for medical rubber products (e.g., syringe gaskets, vial plugs, and the like) to be delivered in a state of guaranteeing sterilization thereof, i.e., to be ready-to-use (RTU). Examples of a method for guaranteeing sterilization include methods involving sterilization with high-pressure steam, sterilization with ethylene oxide gas (EOG), and sterilization with gamma ray. The method involving sterilization with gamma ray can effectuate that a medical rubber product can be sterilized while being packaged and thus can be delivered without opening the package. Sterilization with EOG is another way to sterilize a medical rubber product.

The method involving sterilization with gamma ray implements sterilization by means of absorbed dose setting and actually measured values. If a plurality of medical rubber parts are packed into a packaging bag and sterilization with gamma ray is performed, unevenness among the medical rubber parts might occur in the packaging bag. Thus, even when the packaging bag is irradiated with a predetermined radiation dose of gamma ray, variation in the absorbed dose of gamma ray can occur in the packaging bag. This can give rise to: medical rubber parts having low absorbed doses of gamma ray; and medical rubber parts having high absorbed doses of gamma ray. However, it may be desirable or necessary to ensure, for each medical rubber part, a minimum absorbed dose with which the medical rubber part can be sterilized. Thus, it may be desirable or necessary to irradiate the packaging bag with at least the minimum absorbed dose of gamma ray. This can give rise to medical rubber parts that absorb an excessive dose of gamma ray at the time of sterilization with gamma ray, in the packaging bag.

Japanese Laid-Open Patent Publication No. 2002-301133 describes: a rubber composition containing an isobutylene copolymer as a main component and having a density not higher than 0.95, the rubber composition being used for a medical rubber plug or a medical rubber product on which radiation treatment is easily performed; and a crosslinked product of the rubber composition.

Japanese Laid-Open Patent Publication (Translation of PCT Application) No. 2017-531604 describes a method for packaging a part (1), made from an elastomer, such as a plug for a pharmaceutical agent container. The method includes: a step of packing the part (1) into a primary bag (10) made from a material substantially impermeable with air; and a step of applying an atmosphere with at least 80% of nitrogen to the inside of the primary bag (10). In the method, the primary bag (10) is put in a secondary bag (20), and the interval between the primary bag (10) and the secondary bag (20) is set to be in a vacuum state.

When a medical rubber part is sterilized by being irradiated with gamma ray, cleavage and crosslinking simultaneously can occur in a polymer forming the medical rubber part. If an excessive dose of gamma ray is absorbed, cleavage of the main chain of the polymer forming the medical rubber part may be promoted, whereby low-molecular-weight components can be generated. Consequently, the non-elution characteristics of the medical rubber part having been subjected to sterilization with gamma ray may deteriorate. In addition, bleed-out, onto a surface of the rubber part, of the low-molecular-weight components resulting from the cleavage may occur, and medical rubber parts may come into close contact with each other. Consequently, a trouble of clogging in a parts feeder used in a manufacturing process for medical products may occur.

SUMMARY

A medical rubber composition according to one or more embodiments of the present disclosure can comprise or contain:

- a (a) base polymer containing a halogenated isobutylene-isoprene rubber;
- a (b) polyethylene; and
- a (c) triazine derivative as a crosslinking agent, wherein
- a proportion of the triazine derivative contained per 100% by mole of a halogen of the halogenated isobutylene-isoprene rubber contained in the (a) base polymer is 1% by mole to 15% by mole.

DETAILED DESCRIPTION

Figure 1:
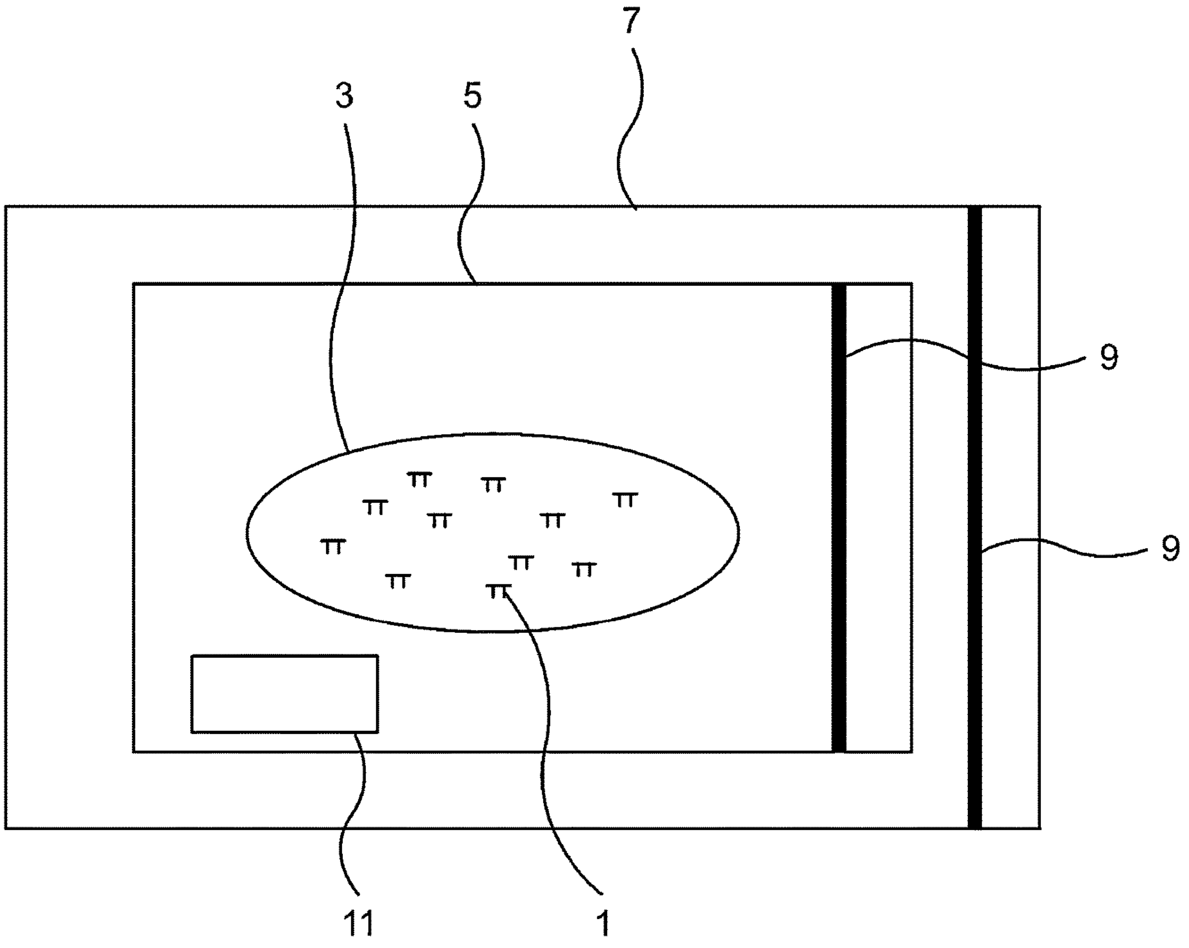
FIG. 1 is a diagram for schematically explaining an exemplary packaging mode for a medical rubber part according to one or more embodiments of the present disclosure.

The present disclosure has been made at least in view of the above circumstances in the Background section, and an object of the present disclosure, among one or more objects, can be to provide: a medical rubber part in which non-elution characteristics can be maintained even after sterilization with gamma ray and which can experience less trouble in a manufacturing process for the medical product; a packaging article for the medical rubber part; and a medical rubber composition for manufacturing the medical rubber part.

A medical rubber composition of the present disclosure can comprise or contain: a (a) base polymer containing a halogenated isobutylene-isoprene rubber; a (b) polyethylene; and a (c) triazine derivative as a crosslinking agent, wherein a proportion of the (c) triazine derivative contained per 100% by mole of a halogen of the halogenated isobutylene-isoprene rubber contained in the (a) base polymer can be 1% by mole to 15% by mole.

Firstly, the (a) base polymer containing a halogenated isobutylene-isoprene rubber used in the present disclosure will be described. Examples of the halogenated isobutylene-isoprene rubber can include: chlorinated isobutylene-isoprene rubber; brominated isobutylene-isoprene rubber; a bromide of a copolymer rubber of isobutylene and p-methylstyrene (brominated isobutylene-para-methylstyrene copolymer rubber); and the like.

As the halogenated isobutylene-isoprene rubber, a chlorinated isobutylene-isoprene rubber or a brominated isobutylene-isoprene rubber can be preferable. The chlorinated isobutylene-isoprene rubber or the brominated isobutylene-isoprene rubber can be obtained by, for example, causing a reaction in which: chlorine or bromine is added to an isoprene structural moiety (specifically, a double bond and/or a carbon atom adjacent to the double bond) in an isobutylene-isoprene rubber; or the isoprene structural moiety is substituted with chlorine or bromine. The isobutylene-isoprene rubber can be a copolymer obtained by polymerizing isobutylene and a small amount of isoprene.

The halogen content of the halogenated isobutylene-isoprene rubber can be preferably not lower than 0.5% by mass, more preferably not lower than 1% by mass, and further preferably not lower than 1.5% by mass. Meanwhile, the halogen content can be preferably not higher than 5% by mass, more preferably not higher than 4% by mass, and further preferably not higher than 3% by mass.

Specific examples of the chlorinated isobutylene-isoprene rubber can include at least one of: CHLOROBUTYL 1066 [stabilizer: NS, halogen content: 1.26%, Mooney viscosity: 38 $ML_{1+8}$ (125° C.), specific gravity: 0.92] manufactured by JAPAN BUTYL Co., Ltd.; LANXESS X_BUTYL CB1240 manufactured by LANXESS; and the like.

Specific examples of the brominated isobutylene-isoprene rubber can include at least one of: BROMOBUTYL 2255 [stabilizer: NS, halogen content: 2.0%, Mooney viscosity: 46 ML1+8 (125° C.), specific gravity: 0.93] manufactured by JAPAN BUTYL Co., Ltd.; LANXESS X_BUTYL BBX2 manufactured by LANXESS; and the like.

The (a) base polymer may contain a rubber component other than halogenated isobutylene-isoprene rubber. Examples of the other rubber component can include butyl-based rubbers, isoprene rubber, butadiene rubber, styrene-butadiene rubber, natural rubber, chloroprene rubber, nitrile-based rubbers such as acrylonitrile-butadiene rubber, hydrogenated nitrile-based rubbers, norbornene rubber, ethylene-propylene rubber, ethylene-propylene-diene rubber, acrylic rubber, ethylene-acrylate rubber, fluororubber, chlorosulfonated polyethylene rubber, epichlorohydrin rubber, silicone rubber, urethane rubber, polysulfide rubber, phosphazene rubber, 1,2-polybutadiene, and the like. These rubber components may be used singly, or two or more of these rubber components may be used in combination.

In the case of using the other rubber component, the proportion of the halogenated isobutylene-isoprene rubber contained in the (a) base polymer can be preferably not lower than 90% by mass, more preferably not lower than 95% by mass, and further preferably not lower than 98% by mass. A mode in which the (a) base polymer contains only the halogenated isobutylene-isoprene rubber can also be preferable.

The medical rubber composition according to one or more embodiments of the present disclosure can comprise or contain the (b) polyethylene. The polyethylene can be more likely to absorb gamma ray than the (a) base polymer is. Thus, the polyethylene can have an effect of preventing cleavage of chains of the (a) base polymer due to irradiation with the gamma ray. In addition, a polyethylene having a low degree of crystallinity can have a branched chain, and it can be considered that crosslinking progresses without cleavage of the main chain even upon irradiation with the gamma ray. As a result, the non-elution characteristics of the medical rubber composition can be considered to be improved.

From this viewpoint, examples of the (b) polyethylene to be used in the present disclosure can include high-density polyethylene (HDPE) and low-density polyethylene (LDPE). The high-density polyethylene (HDPE) and the low-density polyethylene (LDPE) may be used singly, or the high-density polyethylene (HDPE) and the low-density polyethylene (LDPE) may be used in combination.

In the case of using the high-density polyethylene (HDPE) and the low-density polyethylene (LDPE) in combination, the mass ratio (HDPE/LDPE) of the high-density polyethylene (HDPE) to the low-density polyethylene (LDPE) can be preferably not lower than 0.3, more preferably not lower than 0.5, and further preferably not lower than 1.0. Meanwhile, the mass ratio (HDPE/LDPE) can be preferably not higher than 5.0, more preferably not higher than 4.0, and further preferably not higher than 3.0. The reason for this can be because, if the mass ratio (HDPE/LDPE) of the high-density polyethylene (HDPE) to the low-density polyethylene (LDPE) falls within the aforementioned range, a radical absorption effect at the time of irradiation with the gamma ray and an appropriate hardness of the rubber can be ensured.

The (b) polyethylene can preferably contain or comprise a polyethylene having a degree of crystallinity not higher than 70%.

The degree of crystallinity of the high-density polyethylene (HDPE) can be preferably 60% to 80%, more preferably 60% to 75%, and further preferably 60% to 70%. The degree of crystallinity of the low-density polyethylene (LDPE) can be preferably 30% to 50%, more preferably 30% to 45%, and further preferably 30% to 40%. The reason for this can be because, if the degree of crystallinity of the polyethylene falls within the aforementioned range, radicals generated by irradiation with the gamma ray are effectively absorbed, and cleavage of the main chain of the polymer can be prevented.

The degree of crystallinity of the (b) polyethylene can be determined according to the following expression.

Degree of crystallinity (%)=(measured melting heat quantity (J/g)/perfect crystal melting heat quantity (J/g))×100

The perfect crystal melting heat quantity (J/g) can be 293 J/g (a value in a literature) and can be a melting heat quantity of the polyethylene at 100%-crystallinity. A measurement method for the melting heat quantity of the polyethylene will be described later.

As the (b) polyethylene, the low-density polyethylene can be preferable. The density ($g/cm^3$) of the high-density polyethylene can be preferably 0.930 to 0.960 and more preferably 0.930 to 0.950. The density ($g/cm^3$) of the low-density polyethylene may not be particularly limited, but can be preferably 0.910 to 0.925 and more preferably 0.910 to 0.920.

As the (b) polyethylene, a polyethylene in the form of fine powder can be preferably used. The volume-average particle diameter of the polyethylene in the form of fine powder can be preferably not smaller than 10 μm, more preferably not smaller than 15 μm, and further preferably not smaller than 20 μm. Meanwhile, the volume-average particle diameter can be preferably not larger than 200 μm, more preferably not larger than 160 μm, and further preferably not larger than 120 μm. The reason for this can be because, if the average particle diameter of the polyethylene in the form of fine powder falls within the aforementioned range, it can become easy for the polyethylene to be evenly mixed or dispersed in the polymer.

The blending amount of the (b) polyethylene per 100 parts by mass of the (a) base polymer can be preferably not smaller than 3 parts by mass, more preferably not smaller than 5 parts by mass, and further preferably not smaller than 10 parts by mass. Meanwhile, the blending amount can be preferably not larger than 30 parts by mass, more preferably not larger than 25 parts by mass, and further preferably not larger than 20 parts by mass. The reason for this can be because, if the blending amount of the (b) polyethylene falls within the aforementioned range, radicals generated at the time of irradiation with the gamma ray can be effectively absorbed, and cleavage of the main chain of the polymer can be prevented.

The medical rubber composition of the present disclosure can preferably contain or comprise a triazine derivative as the (c) crosslinking agent.

The triazine derivative can act as a crosslinking agent on the halogenated isobutylene-isoprene rubber. Examples of the triazine derivative can include a compound represented by a general formula (1).

[Chem.1]

(1)

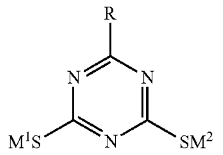

[In the formula, R represents —SH, —$OR^1$, —$SR^2$, —$NHR^3$, or —$NR^4R^5$ ($R^1$, $R^2$, $R^3$, $R^4$, and $R^5$ can each represent an alkyl group, an alkenyl group, an aryl group, an aralkyl group, an alkylaryl group, or a cycloalkyl group. $R^4$ and $R^5$ may be identical to each other or different from each other.). $M^1$ and $M^2$ can each represent H, Na, Li, K, ½Mg, ½Ba, ½Ca, an aliphatic primary, secondary, or tertiary amine, a quaternary ammonium salt, or a phosphonium salt. $M^1$ and $M^2$ may be identical to each other or different from each other.]

In the general formula (1), examples of the alkyl group can include alkyl groups having 1 to 12 carbon atoms, such as a methyl group, an ethyl group, an n-propyl group, an isopropyl group, an n-butyl group, an isobutyl group, a tert-butyl group, an n-pentyl group, an isopentyl group, a tert-pentyl group, an n-hexyl group, a 1,1-dimethylpropyl group, an octyl group, an isooctyl group, a 2-ethylhexyl group, a decyl group, and a dodecyl group. Examples of the alkenyl group can include alkenyl groups having 1 to 12 carbon atoms, such as a vinyl group, an allyl group, a 1-propenyl group, an isopropenyl group, a 2-butenyl group, a 1,3-butadienyl group, and a 2-pentenyl group. Examples of the aryl group can include monocyclic aromatic hydrocarbon groups and condensed polycyclic aromatic hydrocarbon groups, and examples thereof can include: aryl groups having 6 to 14 carbon atoms, such as a phenyl group, a naphthyl group, an anthryl group, a phenanthryl group, and an acenaphthylenyl group; and the like. Examples of the aralkyl group can include aralkyl groups having 7 to 19 carbon atoms, such as a benzyl group, a phenethyl group, a diphenylmethyl group, a 1-naphthylmethyl group, a 2-naphthylmethyl group, a 2,2-diphenylethyl group, a 3-phenylpropyl group, a 4-phenylbutyl group, a 5-phenylpentyl group, a 2-biphenylylmethyl group, a 3-biphenylylmethyl group, and a 4-biphenylylmethyl group. Examples of the alkylaryl group can include alkylaryl groups having 7 to 19 carbon atoms, such as a tolyl group, a xylyl group, and an octylphenyl group. Examples of the cycloalkyl group can include: cycloalkyl groups having 3 to 9 carbon atoms, such as a cyclopropyl group, a cyclobutyl group, a cyclopentyl group, a cyclohexyl group, a cycloheptyl group, a cyclooctyl group, and a cyclononyl group; and the like.

Specific examples of the triazine derivative represented by the general formula (1) can include 2,4,6-trimercapto-s-triazine, 2-methylamino-4,6-dimercapto-s-triazine, 2-(n-butylamino)-4,6-dimercapto-s-triazine, 2-octylamino-4,6-dimercapto-s-triazine, 2-propylamino-4,6-dimercapto-s-triazine, 2-diallylamino-4,6-dimercapto-s-triazine, 2-dimethylamino-4,6-dimercapto-s-triazine, 2-dibutylamino-4,6-dimercapto-s-triazine, 2-di(iso-butylamino)-4,6-dimercapto-s-triazine, 2-dipropylamino-4,6-dimercapto-s-triazine, 2-di(2-ethylhexyl)amino-4,6-dimercapto-s-triazine, 2-dioleylamino-4,6-dimercapto-s-triazine, 2-laurylamino-4,6-dimercapto-s-triazine, 2-anilino-4,6-dimercapto-s-triazine, and sodium salts and disodium salts thereof.

Among these triazine derivatives, 2,4,6-trimercapto-s-triazine, 2-dialkylamino-4,6-dimercapto-s-triazine, and 2-anilino-4,6-dimercapto-s-triazine are preferable, and 2-dibutylamino-4,6-dimercapto-s-triazine can be particularly preferable since 2-dibutylamino-4,6-dimercapto-s-triazine may be relatively easy to obtain.

Other examples of the triazine derivative can include one or more of 6-[bis(2-ethylhexyl)amino]-1,3,5-triazine-2,4-dithiol, 6-diisobutylamino-1,3,5-triazine-2,4-dithiol, 6-dibutylamino-1,3,5-triazine-2,4-dithiol, 6-dibutylamino-1,3,5-triazine-2,4-dithiol monosodium, 6-anilino-1,3,5-triazine-2,4-dithiol, 1,3,5-triazine-2,4,6-trithiol, and the like.

According to one or more embodiments of the present disclosure, these triazine derivatives may be used singly, or two or more of these triazine derivatives may be used in combination.

In the medical rubber composition of the present disclosure, the proportion of the triazine derivative contained per 100% by mole of the halogen of the halogenated isobutylene-isoprene rubber contained in the (a) base polymer can be preferably not lower than 1% by mole, more preferably not lower than 5% by mole, further preferably not lower than 8% by mole, and even further preferably not lower than 10% by mole. Meanwhile, the proportion can be preferably not higher than 15% by mole and more preferably not higher than 12% by mole. If the proportion of the triazine derivative falls within the aforementioned range, no triazine derivative remains as a residual triazine derivative in the rubber composition after vulcanization, and the entire triazine derivative can be used for crosslink bonds, whereby favorable rubber physical properties (hardness, tensile properties, Cset) and favorable non-elution characteristics can be obtained.

In the medical rubber composition of the present disclosure, the amount of the (c) triazine derivative contained per 100 parts by mass of the (a) base polymer component can be preferably not smaller than 0.1 parts by mass and more preferably not smaller than 0.5 parts by mass. Meanwhile, the amount can be preferably not larger than 1.4 parts by mass and more preferably not larger than 1.2 parts by mass. The reason for this can be because, if the amount of the (c) triazine derivative falls within the aforementioned range, a rubber having favorable rubber physical properties (hardness, tensile properties, Cset) and good processability (less susceptibility to scorching) can be obtained.

The medical rubber composition according to one or more embodiments of the present disclosure can preferably contain no vulcanization accelerator. That is, one or more embodiments of the disclosed subject matter can be free of or without any vulcanization accelerator. The reason for this is because a vulcanization accelerator could remain in a rubber product obtained as a final product and could elute into a drug solution inside a syringe or a vial. Examples of the vulcanization accelerator can include guanidine-based accelerators (e.g., diphenylguanidine), thiuram-based accelerators (e.g., tetramethylthiuram disulfide and tetramethylthiuram monosulfide), dithiocarbamate-based accelerators (e.g., zinc dimethyldithiocarbamate), thiazole-based accelerators (e.g., 2-mercaptobenzothiazole and dibenzothiazyl disulfide), and sulfenamide-based accelerators (N-cyclohexyl-2-benzothiazole sulfenamide and N-t-butyl-2-benzothiazole sulfenamide).

The medical rubber composition according to one or more embodiments of the present disclosure may contain or comprise a hydrotalcite. The hydrotalcite can function as an anti-scorching agent upon crosslinking in the halogenated isobutylene-isoprene rubber and can also have a function of preventing increase in permanent strain upon compression in the medical rubber part. Further, the hydrotalcite can also function as an acid acceptor for absorbing chlorine-based gas and bromine-based gas, which have been generated upon crosslinking in the halogenated isobutylene-isoprene rubber, and preventing occurrence of, for example, crosslinking inhibition due to these gases. Magnesium oxide can also function as an acid acceptor.

Examples of the hydrotalcite can include one or more of Mg-Al-based hydrotalcites such as $Mg_{4.5}Al_2(OH)_{13}CO_3 \cdot 3.5H_2O$, $Mg_{4.5}Al_2(OH)_{13}CO_3$, $Mg_4Al_2(OH)_{12}CO_3 \cdot 3.5H_2O$, $Mg_6Al_2(OH)_{16}CO_3 \cdot 4H_2O$, $Mg_5Al_2(OH)_{14}CO_3 \cdot 4H_2O$, and $Mg_3Al_2(OH)_{10}CO_3 \cdot 1.7H_2O$, and the like.

Specific examples of the hydrotalcite can include DHT-4A (registered trademark)-2 manufactured by Kyowa Chemical Industry Co., Ltd., and the like.

In the case where a hydrotalcite is used as an acid acceptor in the medical rubber composition, the hydrotalcite can be preferably used in combination with MgO. In this case, the blending amount of the hydrotalcite can be preferably considered in terms of the total amount of the acid acceptors (hydrotalcite and MgO). The total amount of the acid acceptors (hydrotalcite and MgO) contained per 100 parts by mass of the (a) base polymer component can be preferably not smaller than 0.5 parts by mass and more preferably not smaller than 1 part by mass. Meanwhile, the total amount can be preferably not larger than 15 parts by mass and more preferably not larger than 10 parts by mass. The reason for this can be because, if the total amount of the acid acceptors (hydrotalcite and MgO) falls within the aforementioned range, generation of rust on a mold or the like can be suppressed, and defects that raw materials themselves turn into a white-spotted unwanted object can be reduced.

The medical rubber composition according to one or more embodiments of the present disclosure may contain or comprise a co-crosslinking agent. The co-crosslinking agent can be preferably a polyfunctional (meth)acrylate compound. The polyfunctional (meth)acrylate compound can be more preferably a difunctional or higher-functional (meth) acrylate-based compound and further preferably a trifunctional or higher-functional (meth)acrylate-based compound. Meanwhile, the polyfunctional (meth)acrylate compound can be preferably an octafunctional or lower-functional (meth)acrylate-based compound and more preferably a hexafunctional or lower-functional (meth)acrylate-based compound. Examples of the difunctional or higher-functional (meth)acrylate compound can include a compound having at least two acryloyl groups and/or methacryloyl groups. The term "(meth)acrylate" can mean or be regarded as "acrylate" and/or "methacrylate."

Examples of the difunctional or higher-functional (meth) acrylate-based compound can include di(meth)acrylate of polyethylene glycol, 1,4-butanediol di(meth)acrylate, 1,6-hexanediol di(meth)acrylate, 1,9-nonanediol di(meth)acrylate, trimethylolpropane tri(meth)acrylate, trimethylolethane tri(meth)acrylate, pentaerythritol tri(meth)acrylate, pentaerythritol tetra(meth)acrylate, glycerin tri(meth)acrylate, dipentaerythritol tri(meth)acrylate, dipentaerythritol tetra (meth)acrylate, dipentaerythritol penta(meth)acrylate, dipentaerythritol hexa(meth)acrylate, tripentaerythritol tetra (meth)acrylate, tripentaerythritol penta(meth)acrylate, tripentaerythritol hexa(meth)acrylate, tripentaerythritol hepta (meth)acrylate, and the like. These co-crosslinking agents may be used singly, or two or more of these co-crosslinking agents may be used in combination.

In the medical rubber composition according to one or more embodiments of the present disclosure, a (d) filler may be blended. Examples of the (d) filler can include inorganic fillers such as silica, clay, and talc. The filler can be further preferably clay or talc. The filler can have a function of adjusting the rubber hardness of the medical rubber part and/or can function also as an extender for reducing manufacturing cost for the medical rubber part.

Examples of the clay can include calcined clay and kaolin clay. Specific examples of the clay can include SILLITIN (registered trademark) Z manufactured by Hoffmann Mineral GmbH, SATINTONE (registered trademark) W manufactured by Engelhard Corporation, NN kaolin clay manufactured by Tsuchiya Kaolin Industry Co., Ltd., PoleStar200R manufactured by Imerys Specialties Japan Co., Ltd., and the like.

Specific examples of the talc can include High toron A manufactured by Takehara Kagaku Kogyo Co., Ltd., MICRO ACE (registered trademark) K-1 manufactured by Nippon Talc Co., Ltd., MISTRON (registered trademark) Vapor manufactured by Imerys Specialties Japan Co., Ltd., and the like.

In the medical rubber composition according to one or more embodiments of the present disclosure, a colorant such as titanium oxide or carbon black, polyethylene glycol as a processing aid or as a crosslinking activator, a plasticizer (for example, paraffin oil), and the like may further be blended in appropriate proportions.

One or more embodiments of the present disclosure can encompass a medical rubber part molded from the medical rubber composition. Examples of the medical rubber part of the present disclosure can include: rubber plugs and sealing members of containers (for example, vials) for various medical preparations such as a liquid preparation, a powder preparation, and a freeze-dried preparation; rubber plugs for vacuum blood collection tubes; slidable parts and sealing parts such as plunger stoppers and nozzle caps for pre-filled syringes; and the like.

The medical rubber composition according to one or more embodiments of the present disclosure can be obtained by kneading the (a) base polymer containing the halogenated isobutylene-isoprene rubber, the (b) polyethylene, the (c) triazine derivative as a crosslinking agent, and other blending materials to be added as necessary. The kneading can be performed by using, for example, an open roll, a sealed-type kneader, or the like. The kneaded product can be preferably molded in the shape of a ribbon, the shape of a sheet, the shape of a pellet, or the like, and is more preferably molded in the shape of a sheet.

If the kneaded product having the shape of a ribbon, the shape of a sheet, or the shape of a pellet is press-molded, as examples, a medical rubber part having a desired shape can be obtained. A crosslinking reaction in the medical rubber composition can progress during the pressing. The temperature in the molding can be, for example, preferably not lower than 130° C. and more preferably not lower than 140° C. Meanwhile, the temperature can be preferably not higher than 200° C. and more preferably not higher than 190° C. The time for the molding can be preferably not shorter than 2 minutes and more preferably not shorter than 3 minutes. Meanwhile, the time can be preferably not longer than 60 minutes and more preferably not longer than 30 minutes. The pressure for the molding can be preferably not lower than 0.1 MPa and more preferably not lower than 0.2 MPa. Meanwhile, the pressure can be preferably not higher than 10 MPa and more preferably not higher than 8 MPa.

Unnecessary portions may be cut off and removed from the molded product after the press-molding, such that the molded product can have a predetermined shape. The obtained molded product can be cleaned, dried, and packaged to manufacture the medical rubber part.

In addition, a resin film may be stacked on and integrated with the medical rubber part. Examples of the resin film can include films made from inactive resins such as polytetrafluoroethylene (PTFE), tetrafluoroethylene-ethylene copolymer (ETFE), modified products thereof, and ultrahigh-molecular-weight polyethylene (UHMWPE).

The resin film may only have to be, for example, press-molded in a state of being superposed on the rubber composition having the shape of a sheet such that the resin film is integrated with the medical rubber part formed after the press-molding.

Embodiments of the present disclosure can also encompass a packaging article for the medical rubber part of the present disclosure, where the packaging article can accommodate a plurality of the medical rubber parts, wherein the packaging article can have been subjected to sterilization treatment with gamma ray.

Examples of the gamma ray can include gamma rays emitted from cobalt-60, cesium-137, and the like. Gamma ray emitted from cobalt-60 may be preferable.

Regarding irradiation with the gamma ray, an absorbed dose of the gamma ray for the medical rubber part can be set through an actual sterilization validation procedure. For ordinary medical devices, operation can be performed with a minimum absorbed dose being set to 15 kGy in many cases, as an example. A radiation dose, of the gamma ray, at which the absorbed doses of the gamma ray in all of the medical rubber parts in the packaging article take values not lower than 15 kGy, can vary, for instance, depending on the number of the medical rubber parts in the packaging article, the manner in which the medical rubber parts are put into the packaging article, and/or the like. In general, irradiation can be performed in a dose that falls within a range of not lower than 1.4 times 15 kGy and not higher than 2.0 times 15 kGy. Likewise, if the minimum absorbed dose is set to 20 kGy, irradiation can be performed in a dose that falls within a range of not lower than 1.4 times 20 kGy and not higher than 2.0 times 20 kGy, and, if the minimum absorbed dose is set to 25 kGy, irradiation can be performed in a dose that falls within a range of not lower than 1.4 times 25 kGy and not higher than 2.0 times 25 kGy. The absorbed dose of the gamma ray can be ascertained by attaching a dosemeter to an object that is to be irradiated.

The oxygen concentration in the packaging article for accommodating the medical rubber parts not having yet been subjected to sterilization treatment with the gamma ray can be preferably not higher than 5%, more preferably not higher than 3%, and further preferably not higher than 1%. The reason for this can be because, if the oxygen concentration in the packaging article is set to be not higher than 5%, degradation of the (a) base polymer due to irradiation with the gamma ray can be suppressed.

Examples of a method for setting the oxygen concentration in the packaging article to be not higher than 5% can include: a method in which air in the packaging article is substituted with an inert gas; and a method in which an oxygen adsorber is accommodated in the packaging article.

Examples of the inert gas can include: rare gases such as helium gas, neon gas, and argon gas; nitrogen gas; and the like.

Examples of the oxygen adsorber can include AGELESS (commercially available product) which is an iron-based oxygen adsorber, and the like.

The packaging article for accommodating the medical rubber part may not be particularly limited as long as the packaging article allows irradiation with the gamma ray. Examples of the form of the packaging article can include the forms of a bag, a box, and the like.

Examples of the packaging bag can include packaging bags formed of a thermoplastic resin film made from polyethylene, polyamide, or polyester. The packaging bag can be preferably one that can be sealed. The box may not be particularly limited, and examples of the box can include a box made from paper, a box made from cardboard, and the like.

Examples of the packaging article can include: a packaging article having gas permeability; and a packaging article having non-gas permeability (gas sealability). It may also be preferable to use these packaging articles in combination.

Sterilization of the medical rubber part with the gamma ray may be performed on, for example, a packaging article (for example, a cardboard box) in which, with a plurality of the medical rubber parts being accommodated in a primary packaging article (for example, packaging bag), a plurality of the primary packaging articles can be further accommodated.

FIG. 1 is a diagram for schematically explaining an exemplary packaging mode for irradiation with the gamma ray according to one or more embodiments of the present disclosure. In the mode shown in FIG. 1, a primary packaging article 3, which can accommodate a plurality of medical rubber parts 1, can be further accommodated in a secondary static charge prevention packaging article 5 and a tertiary static charge prevention packaging article 7. As the primary packaging article 3, a packaging article having gas permeability can be preferable. As the secondary static charge prevention packaging article 5 and/or the tertiary static charge prevention packaging article 7, packaging articles capable of sealing gas can be preferable. Each of the secondary static charge prevention packaging article 5 and/or the tertiary static charge prevention packaging article 7 can be preferably sealed with a heat seal 9. In the case of using an oxygen adsorber 11, the oxygen adsorber 11 can be preferably disposed between the primary packaging article 3 and the secondary packaging article 5 such that the oxygen adsorber 11 does not come into direct contact with the medical rubber parts 1. By disposing the oxygen adsorber 11 in the secondary packaging article 5, the oxygen concentration in each of the secondary packaging article 5 and the primary packaging article 3 can be set to be not higher than 5%. Irradiation with the gamma ray can be performed with a plurality of the tertiary static charge prevention packaging articles 7 being accommodated in a quaternary packaging article (for example, a cardboard box).

Figure 2:
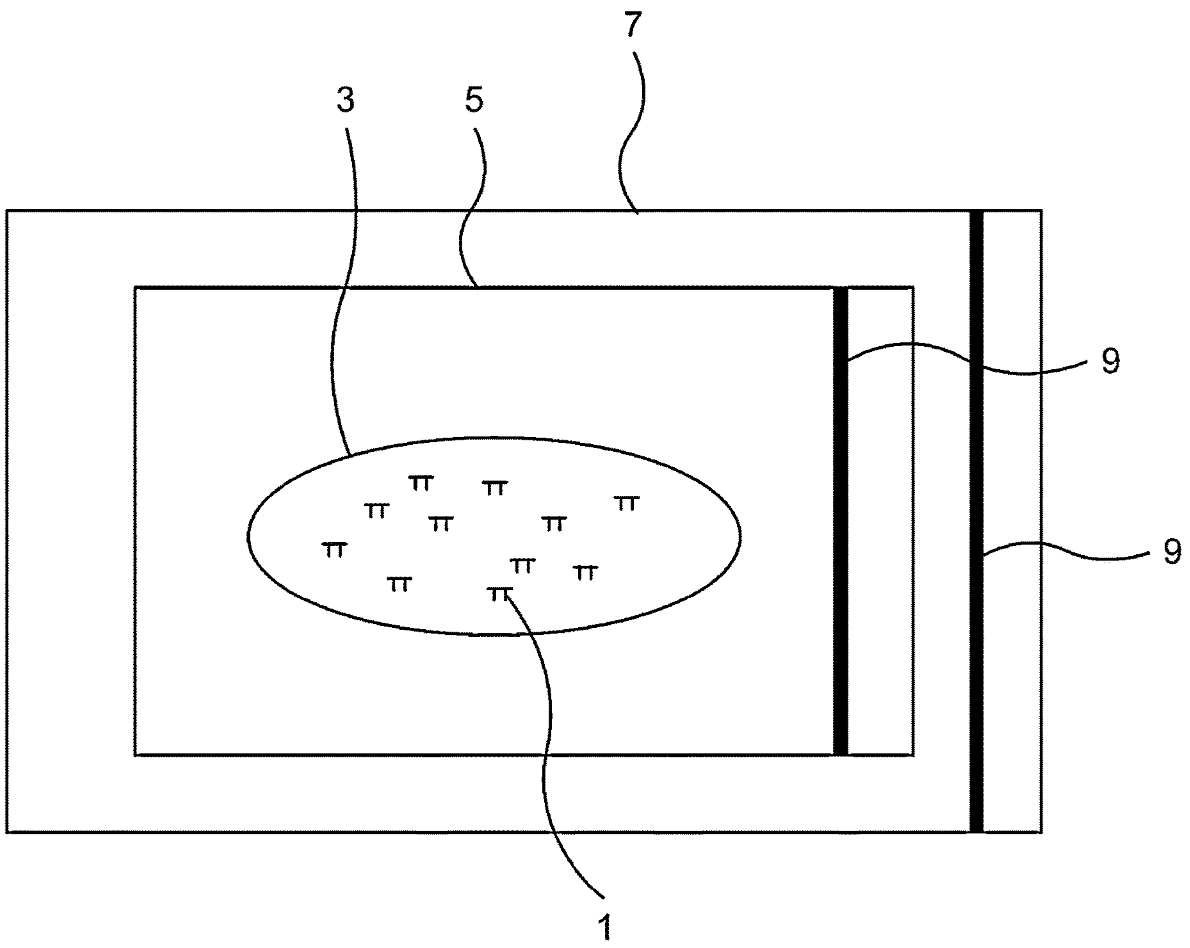
FIG. 2 is a diagram for schematically explaining another exemplary packaging mode for the medical rubber part according to one or more embodiments of the present disclosure.

FIG. 2 is a diagram for schematically explaining another exemplary packaging mode for irradiation with the gamma ray according to one or more embodiments of the disclosed subject matter. In the mode shown in FIG. 2, the primary packaging article 3, which can accommodate the plurality of medical rubber parts 1, can be further accommodated in the secondary static charge prevention packaging article 5 and the tertiary static charge prevention packaging article 7. Each of the secondary static charge prevention packaging article 5 and/or the tertiary static charge prevention packaging article 7 can be preferably sealed with the heat seal 9. As the primary packaging article 3, a packaging article having gas permeability can be preferable. As the secondary static charge prevention packaging article 5 and/or the tertiary static charge prevention packaging article 7, packaging articles capable of sealing gas can be preferable. The secondary packaging article 5 accommodating the primary packaging article 3 can be filled with an inert gas. The filling with the inert gas can make it possible to set the oxygen concentration in each of the secondary packaging article 5 and the primary packaging article 3 to be not higher than 5%. Irradiation with the gamma ray can be performed with a plurality of the tertiary static charge prevention packaging articles 7 being accommodated in a quaternary packaging article (for example, a cardboard box).

At the time of irradiation with the gamma ray, irradiation with the gamma ray can be preferably performed in a state where the packaging article accommodating the plurality of medical rubber parts is accommodated in, for example, an accommodation container made from an aluminum alloy.

EXAMPLES

Hereinafter, the present disclosure will be described in detail by means of examples, but the present disclosure is not limited to the following examples, and any of modifications and implementation modes made within the scope of the gist of the present disclosure is included in the scope of the present disclosure.

[Preparation of Medical Rubber Compositions]

Rubber compositions were each prepared by blending components other than the crosslinking component among the components indicated in Table 1, kneading the resultant mixture with use of a 10-L pressurization-type sealed kneader at a filling rate of 75%, aging the kneaded product at room temperature, then, adding the crosslinking component to the kneaded product, and kneading the resultant mixture with use of an open roll.

[Manufacturing of Medical Rubber Plugs]

Each of the aforementioned rubber compositions was molded in the shape of a sheet, sandwiched between an upper mold portion and a lower mold portion, and press-molded in a vacuum at 180° C. for 10 minutes. Consequently, a plurality of rubber plugs of vials for a freeze-dried injectable were continuously formed on the above one sheet. In each rubber plug, a flange had a diameter of 19.0 mm, a leg portion had a diameter of 13.2 mm, and a flange piercing portion had a thickness of 2.5 mm. Thereafter, a silicone-based lubricating coat agent was applied on both surfaces of the above sheet. Then, rubber plugs were manufactured through an outer appearance inspection step, a stamping step, a cleaning step, a sterilizing step, a drying step, and a packaging step. Each of the manufactured rubber plugs was used in an eluting material test and a tack test.

TABLE 1

| Medical rubber composition No. | | 1 | 2 | 3 | 4 | 5 |
|---|---|---|---|---|---|---|
| Blending amount (parts by mass) | Chlorinated isobutylene-isoprene rubber | 100 | 100 | 100 | 100 | 100 |
| | Polyethylene 1 (HDPE) | 10 | 10 | 10 | 10 | 10 |
| | Polyethylene 2 (LDPE) | 5 | 5 | 5 | 5 | 5 |
| | Triazine derivative | 0.6 | 1 | 1.4 | 3 | 5 |
| | Talc | 30 | 30 | 30 | 30 | 30 |
| | Synthetic silica | 30 | 30 | 30 | 30 | 30 |

TABLE 1-continued

| Medical rubber composition No. | | 1 | 2 | 3 | 4 | 5 |
|---|---|---|---|---|---|---|
| | Magnesium oxide | 3 | 3 | 3 | 3 | 3 |
| | Carbon black | 0.5 | 0.5 | 0.5 | 0.5 | 0.5 |
| | Titanium oxide | 3 | 3 | 3 | 3 | 3 |
| | Oil | 2 | 2 | 2 | 2 | 2 |
| Number of moles of chlorine in chlorinated isobutylene-isoprene rubber (/100 g) | | 0.0355 | 0.0355 | 0.0355 | 0.0355 | 0.0355 |
| Number of moles of triazine derivative (MW = 272.2) | | 0.0022 | 0.0037 | 0.0051 | 0.0110 | 0.0184 |
| Proportion (% by mole) of triazine derivative to 100% by mole of halogen | | 6.2% | 10.3% | 14.5% | 31.0% | 51.7% |
| Before irradiation | Internal environment of packaging article | Oxygen adsorber contained | Oxygen adsorber contained | Oxygen adsorber contained | Oxygen adsorber contained | Oxygen adsorber contained |
| | Oxygen concentration in packaging article (%) | 0.1% | 0.1% | 0.1% | 0.1% | 0.1% |
| I. Eluting material test | Before irradiation | Pass | Pass | Pass | Pass | Pass |
| | After 25-kGy irradiation | Pass | Pass | Pass | Pass | Not pass |
| | After 50-kGy irradiation | Pass | Pass | Pass | Not pass | Not pass |
| II. TOC test | After 25-kGy irradiation (relative evaluation of post-irradiation value with respect to pre-irradiation value) | 97% | 101% | 114% | 134% | 161% |
| | After 50-kGy irradiation (relative evaluation of post-irradiation value with respect to pre-irradiation value) | 103% | 107% | 127% | 157% | 195% |
| | Evaluation | Good | Good | Slightly good | Bad | Bad |
| III. Tack test | After 25-kGy irradiation (relative evaluation of post-irradiation value with respect to pre-irradiation value) | 90% | 91% | 105% | 110% | 115% |

TABLE 1-continued

| Medical rubber composition No. | | 1 | 2 | 3 | 4 | 5 |
|---|---|---|---|---|---|---|
| | After 50-kGy irradiation (relative evaluation of post-irradiation value with respect to pre-irradiation value) | 95% | 97% | 112% | 122% | 128% |
| | Evaluation | Excellent | Excellent | Good | Slightly good | Slightly good |
| Comprehensive determination as to suitability for being RTU up to 50 kGy | | Suitable | Suitable | Suitable | Unsuitable | Unsuitable |

Details of the blending materials used are as follows.
Butylated rubber: HT-1066 (chlorine content: 1.26% by weight) manufactured by Exxon Mobil Corporation
Polyethylene 1: MIPELON XM-220 (degree of crystallinity: 69%) manufactured by Mitsui Chemicals, Inc.
Polyethylene 2: Flo-thene UF20S (degree of crystallinity: 35%) manufactured by SUMITOMO SEIKA CHEMICALS CO., LTD.
Triazine derivative: ZISNET DB manufactured by SANKYO KASEI CO., LTD.
Talc: MISTRON Vapor manufactured by Imerys Specialties Japan Co., Ltd.
Silica: Nipsil LP manufactured by Tosoh Silica Corporation
Magnesium oxide: MAGSARAT 150s manufactured by Kyowa Chemical Industry Co., Ltd.
Carbon black: DIABLACK G manufactured by Mitsubishi Chemical Holdings Corporation
Titanium oxide: KR-380 manufactured by Titan Kogyo Ltd.
Oil: PW380 manufactured by Idemitsu Kosan Co., Ltd.

[Evaluation Methods]

(1) Measurement of Melting Heat Quantity of Polyethylene

The melting heat quantity of each polyethylene was acquired from a primary test at elevated temperatures through differential scanning calorimetry (DSC).

DSC measurement condition: 20° C. to 200° C., with a rate of temperature elevation being 10° C./min.

(2) Eluting Material Test

Measurement sample: each medical rubber plug was irradiated with the gamma ray so as to have absorbed doses of 25 kGy and 50 kGy, whereby a rubber plug having been irradiated with the gamma ray was manufactured.

The measurement sample was tested according to the method in "Extractable substances" described in "7.03 Test for Rubber Closure for Aqueous Infusions" of the 17th edition of the Japanese Pharmacopoeia. Conditions of passing the test were as follows.

- Properties of test solution: colorless and clear
- Ultraviolet transmissivity: a transmissivity being not lower than 99.0% at each of a wavelength of 430 nm and a wavelength of 650 nm with a layer length of 10 mm
- Ultraviolet absorption spectrum: an absorbance being not higher than 0.20 at a wavelength of 220 nm to 350 nm
- pH: the difference between the test solution and a blank test solution being not larger than 1.0
- Zinc: the absorbance of a sample solution being not higher than the absorbance of a standard solution
- Potassium permanganate reducing substance: not higher than 2.0 mL/100 mL (according to a standard in the Japanese Pharmacopoeia)
- Post-evaporation residue: not larger than 2.0 mg If any of these conditions was not satisfied, the rubber plug was evaluated as "Not pass". Meanwhile, if all of the conditions were satisfied, the rubber plug was evaluated as "Pass".

(3) TOC Test

Regarding the eluting liquid subjected to the eluting material test in "(2)", a total organic carbon value TOC (NPOC: TOC obtained through acidification-aeration treatment) was measured.

- Measurement analysis device: Shimadzu total organic carbon analyzer TOC-VCSH (of a combustion oxidizing type)
- Measurement analysis condition: a combustion tube temperature being 680 degrees with use of a high-sensitivity catalyst
- Carrier gas: highly purified air at 150 mL/min.
- Injection amount: 200 μL
- Concentration of added acid: 1.5%
- Aeration treatment time: 90 sec.

Non-elution characteristics before and after irradiation with the gamma ray were evaluated. The TOC after irradiation with the gamma ray was evaluated by being indicated as a relative index with the TOC before irradiation with the gamma ray being regarded as 100%. A larger numeral means that the non-elution characteristics has deteriorated more relative to the non-elution characteristics before irradiation with the gamma ray.

Evaluation Criteria

- Excellent: not higher than 100% (having been improved relative to a pre-irradiation value)
- Good: higher than 100% and not higher than 120% (approximately equal to the pre-irradiation value)
- Slightly good: higher than 120% and not higher than 150% (having slightly deteriorated relative to the pre-irradiation value)
- Bad: higher than 150% (having deteriorated to a large extent, relative to the pre-irradiation value)

(4) Tack Test

Figure 3:
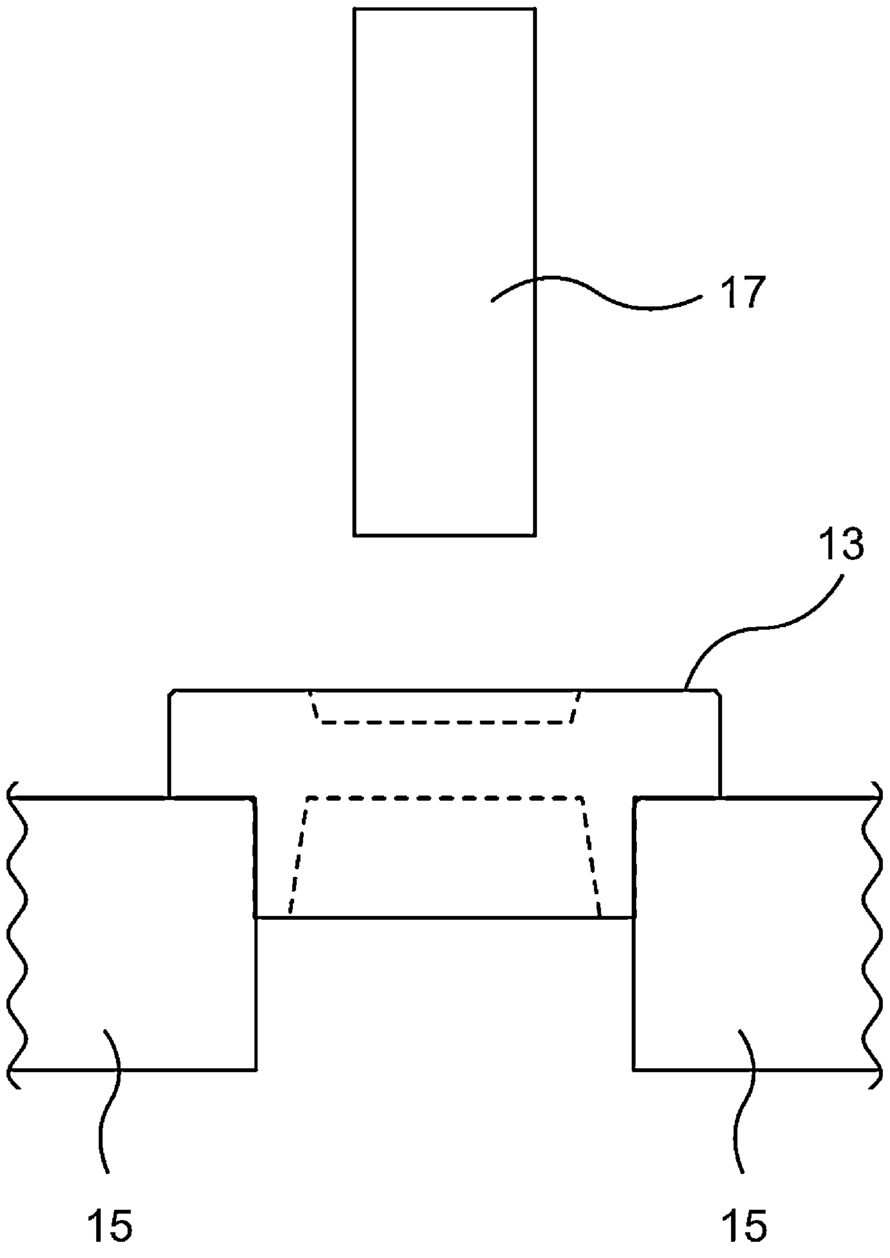
FIG. 3 is a diagram for schematically explaining a tack test method for the medical rubber part according to one or more embodiments of the present disclosure.

A tack test was performed as follows by using a desktop tester EZ-SX available from Shimadzu Corporation. As shown in FIG. 3, a sample 13 was fixed to a fixation jig 15 on the lower side, a metal probe 17 on the upper side was pressed onto the sample 13, and the pressed state was maintained for 10 seconds after the pressure had reached a set value. Thereafter, the metal probe 17 was lifted upward, and a peak value of close contact force generated between the metal probe 17 and the sample 13 was used as a tack value. The measurement was performed 5 times on each sample. From among the measurement values obtained as a result, the maximum value and the minimum value were excluded, and the average value of the remaining three measurement values was calculated. The close contact force of the sample having been irradiated with the gamma ray was indicated as an index with the close contact force of the sample, which had not yet been irradiated with the gamma ray, being regarded as 100. A smaller index indicates a lower tackiness and a more favorable result.

Measurement Conditions

Pressing speed: 0.5 mm/s

Pressing load: 1000 g of weight

Pressed-state maintaining time: 10 seconds

Pull-up speed: 10 mm/s

Ultimate pull-up distance: 3 mm

Diameter of probe: 10 mm

Evaluation Criteria

Excellent: not higher than 100% (having been improved relative to a pre-irradiation value)

Good: higher than 100% and not higher than 120% (approximately equal to the pre-irradiation value)

Slightly good: higher than 120% and not higher than 150% (having slightly deteriorated relative to the pre-irradiation value)

Bad: higher than 150% (having deteriorated to a large extent, relative to the pre-irradiation value)

The results of the eluting material test, the TOC test, and the tack test are indicated together in Table 1.

Determination as to suitability for being ready-to-use was made as follows.

If the result of the eluting material test was "Pass", the result of the TOC test was "Slightly good" or a more favorable evaluation result, and the result of the tack test was "Slightly good" or a more favorable evaluation result, it was determined that suitability for being ready-to-use was attained. Meanwhile, if any of the evaluation results was unfavorable, it was determined that suitability for being ready-to-use was not attained.

From the results in Table 1, it is found that non-elution characteristics are maintained even after sterilization with the gamma ray in each medical rubber part formed from a medical rubber composition. The medical rubber composition contains: a (a) base polymer containing a halogenated isobutylene-isoprene rubber; a (b) polyethylene; and a (c) triazine derivative as a crosslinking agent, wherein a proportion of the triazine derivative contained per 100% by mole of a halogen of the halogenated isobutylene-isoprene rubber contained in the (a) base polymer is 1% by mole to 15% by mole.

The present disclosure makes it possible to provide: a medical rubber part in which non-elution characteristics are maintained even after sterilization with gamma ray and which experiences less troubles in a manufacturing process for the medical product; and a packaging article for the medical rubber part. The present disclosure makes it possible to further provide a medical rubber composition suitable for manufacturing the medical rubber part.

(1) A medical rubber composition according to aspect (1) of the present disclosure is a medical rubber composition containing or comprising:

a (a) base polymer containing a halogenated isobutylene-isoprene rubber;

a (b) polyethylene; and a (c) triazine derivative as a crosslinking agent, wherein a proportion of the triazine derivative contained per 100% by mole of a halogen of the halogenated isobutylene-isoprene rubber contained in the (a) base polymer is 1% by mole to 15% by mole.

(2) A medical rubber composition according to aspect (2) of the present disclosure is the medical rubber composition according to aspect (1) of the present disclosure, wherein the halogenated isobutylene-isoprene rubber is at least one rubber selected from the group consisting of chlorinated isobutylene-isoprene rubber, brominated isobutylene-isoprene rubber, and brominated isobutylene-para-methylstyrene copolymer rubber.

(3) A medical rubber composition according to aspect (3) of the present disclosure is the medical rubber composition according to aspect (1) or (2) of the present disclosure, wherein the (b) polyethylene contains a polyethylene having a degree of crystallinity not higher than 70%.

(4) A medical rubber composition according to aspect (4) of the present disclosure is the medical rubber composition according to any one of aspects (1) to (3) of the present disclosure, wherein a blending amount of the (b) polyethylene per 100 parts by mass of the (a) base polymer is 3 parts by mass to 30 parts by mass.

(5) A medical rubber composition according to aspect (5) of the present disclosure is the medical rubber composition according to any one of aspects (1) to (4) of the present disclosure, wherein an amount of the (c) triazine derivative contained per 100 parts by mass of the (a) base polymer component is not smaller than 0.1 parts by mass and not larger than 1.4 parts by mass.

(6) A medical rubber composition according to aspect (6) of the present disclosure is the medical rubber composition according to any one of aspects (1) to (5) of the present disclosure, wherein the medical rubber composition consists of the (a) base polymer containing the halogenated isobutylene-isoprene rubber, the (b) polyethylene, and the (c) triazine derivative as a crosslinking agent.

(7) A medical rubber composition according to aspect (7) of the present disclosure is the medical rubber composition according to any one of aspects (1) to (6) of the present disclosure, wherein the (a) base polymer consists of the halogenated isobutylene-isoprene rubber.

(8) A medical rubber composition according to aspect (8) of the present disclosure is the medical rubber composition according to any one of aspects (1) to (7) of the present disclosure, wherein the (b) polyethylene has a greater likelihood for absorbing gamma rays compared to the (a) the base polymer.

(9) A medical rubber composition according to aspect (9) of the present disclosure is the medical rubber composition according to any one of aspects (1) to (8) of the present disclosure, wherein the (b) polyethylene contains high-density polyethylene (HDPE) and low-density polyethylene (LDPE) in combination, and a mass ratio (HDPE/LDPE) of the high-density polyethylene (HDPE) to the low-density polyethylene (LDPE) is not lower than 0.3 and not higher than 5.0.

(10) A medical rubber composition according to aspect (10) of the present disclosure is the medical rubber composition according to any one of aspects (1) to (9) of the present disclosure, wherein the (b) polyethylene is in the form of a fine powder having a volume-average particle diameter of not smaller than 10 μm and not larger than 200 μm.

(11) A medical rubber composition according to aspect (11) of the present disclosure is the medical rubber composition according to any one of aspects (1) to (10) of the present disclosure, wherein the medical rubber composition is free of or without any vulcanization accelerator.

(12) A medical rubber composition according to aspect (12) of the present disclosure is the medical rubber composition according to any one of aspects (1) to (11) of the present disclosure, further comprising a hydrotalcite.

(13) A medical rubber composition according to aspect (13) of the present disclosure is the medical rubber composition according to any one of aspects (1) to (12) of the present disclosure, wherein the hydrotalcite is used in combination with MgO.

(14) A medical rubber part according to aspect (14) of the present disclosure is a medical rubber part molded from the medical rubber composition according to any one of aspects (1) to (13) of the present disclosure.

(15) A packaging article, for the medical rubber part, according to aspect (15) of the present disclosure is a packaging article for the medical rubber part according to aspect (14) of the present disclosure, the packaging article accommodating a plurality of the medical rubber parts, wherein the packaging article has been subjected to sterilization treatment with gamma ray.

(16) A packaging article, for the medical rubber part, according to aspect (16) of the present disclosure is the packaging article, for the medical rubber part, according to aspect (15) of the present disclosure, wherein the packaging article has been subjected to sterilization treatment with the gamma ray such that an absorbed dose of the gamma ray is not lower than 15 kGy.

(17) A packaging article, for the medical rubber part, according to aspect (17) of the present disclosure is the packaging article, for the medical rubber part, according to aspect (15) or (16) of the present disclosure, wherein the packaging article has been subjected to sterilization treatment with the gamma ray such that an absorbed dose of the gamma ray is not lower than 25 kGy.

(18) A packaging article, for the medical rubber part, according to aspect (18) of the present disclosure is the packaging article, for the medical rubber part, according to any one of aspects (15) to (17) of the present disclosure, wherein an oxygen concentration in the packaging article not having yet been subjected to sterilization treatment with the gamma ray is not higher than 5%.

(19) A packaging article, for the medical rubber part, according to aspect (19) of the present disclosure is the packaging article, for the medical rubber part, according to any one of aspects (15) to (18) of the present disclosure, wherein the medical rubber part is a rubber plug for a vial, a cap or a plunger stopper for a syringe, or a rubber plug for a vacuum blood collection tube.

What is claimed is:

1. A medical rubber composition comprising:

a (a) base polymer consisting essentially of a halogenated isobutylene-isoprene rubber;

a (b) polyethylene; and a (c) triazine derivative as a crosslinking agent, wherein a proportion of the triazine derivative contained per 100% by mole of a halogen of the halogenated isobutylene-isoprene rubber contained in the (a) base polymer is 1% by mole to 15% by mole, the (b) polyethylene contains high-density polyethylene (HDPE) and low-density polyethylene (LDPE) in combination, and a mass ratio (HDPE/LDPE) of the high-density polyethylene (HDPE) to the low-density polyethylene (LDPE) is not lower than 0.3 and not higher than 5.0.

2. The medical rubber composition according to claim 1, wherein the halogenated isobutylene-isoprene rubber is at least one rubber selected from the group consisting of chlorinated isobutylene-isoprene rubber and brominated isobutylene-isoprene rubber.

3. The medical rubber composition according to claim 1, wherein the (b) polyethylene contains a polyethylene having a degree of crystallinity not higher than 70%.

4. The medical rubber composition according to claim 1, wherein a blending amount of the (b) polyethylene per 100 parts by mass of the (a) base polymer is 3 parts by mass to 30 parts by mass.

5. The medical rubber composition according to claim 1, wherein an amount of the (c) triazine derivative contained per 100 parts by mass of the (a) base polymer component is not smaller than 0.1 parts by mass and not larger than 1.4 parts by mass.

6. The medical rubber composition according to claim 1, wherein the medical rubber composition consists of the (a) base polymer containing the halogenated isobutylene-isoprene rubber, the (b) polyethylene, and the (c) triazine derivative as a crosslinking agent.

7. The medical rubber composition according to claim 1, wherein the (a) base polymer consists of the halogenated isobutylene-isoprene rubber.

8. The medical rubber composition according to claim 1, wherein the (b) polyethylene is in the form of a fine powder having a volume- average particle diameter of not smaller than 10 μm and not larger than 200 μm.

9. The medical rubber composition according to claim 1, wherein the medical rubber composition is free of or without any vulcanization accelerator.

10. The medical rubber composition according to claim 1, further comprising a hydrotalcite.

11. The medical rubber composition according to claim 10, wherein the hydrotalcite is used in combination with MgO.

12. A medical rubber part molded from a medical rubber composition, the medical rubber composition comprising:

a (a) base polymer consisting essentially of a halogenated isobutylene-isoprene rubber;

a (b) polyethylene; and a (c) triazine derivative as a crosslinking agent, wherein a proportion of the triazine derivative contained per 100% by mole of a halogen of the halogenated isobutylene-isoprene rubber contained in the (a) base polymer is 1% by mole to 15% by mole, the (b) polyethylene contains high-density polyethylene (HDPE) and low-density polyethylene (LDPE) in combination, and a mass ratio (HDPE/LDPE) of the high-density polyethylene (HDPE) to the low-density polyethylene (LDPE) is not lower than 0.3 and not higher than 5.0.

13. The medical rubber part according to claim 12, wherein the halogenated isobutylene-isoprene rubber is at least one rubber selected from the group consisting of chlorinated isobutylene-isoprene rubber and brominated isobutylene-isoprene rubber, the (b) polyethylene contains a polyethylene having a degree of crystallinity not higher than 70%, a blending amount of the (b) polyethylene per 100 parts by mass of the (a) base polymer is 3 parts by mass to 30 parts by mass, and/or an amount of the (c) triazine derivative contained per 100 parts by mass of the (a) base polymer component is not smaller than 0.1 parts by mass and not larger than 1.4 parts by mass.

* * * * *